US005877140A

United States Patent [19]

Hardy et al.

[11] Patent Number: 5,877,140

[45] Date of Patent: Mar. 2, 1999

[54] DETERGENT COMPOSITIONS

[76] Inventors: Frederick Edward Hardy, 8 Woodend, Darras Hall, Ponteland, Newcastle upon Tyne NE29 9ES; Barry Thomas Ingram; Christian Leo Marie Vermote, both of Procter & Gamble Ltd., Whitley Road, Longbenton, Newcastle upon Tyne NE12 9TS, all of Great Britain

[21] Appl. No.: 836,296

[22] PCT Filed: Sep. 18, 1995

[86] PCT No.: PCT/US95/11798

§ 371 Date: Mar. 20, 1997

§ 102(e) Date: Mar. 20, 1997

[87] PCT Pub. No.: WO96/09273

PCT Pub. Date: Mar. 28, 1996

[30] Foreign Application Priority Data

Sep. 22, 1994 [GB] United Kingdom .................. 9419115

[51] Int. Cl.[6] ............................... C11D 3/34; C11D 3/20; C07C 305/04; C07C 69/34

[52] U.S. Cl. ......................... 510/351; 510/309; 510/488; 510/491; 510/495; 554/1; 554/90; 554/92; 558/34; 558/266; 558/267; 558/271; 560/150; 560/190

[58] Field of Search .................................... 510/495, 488, 510/351; 558/34, 271

[56] References Cited

U.S. PATENT DOCUMENTS

| | | | |
|---|---|---|---|
| 3,393,213 | 7/1968 | Kiefer et al. | 554/94 |
| 3,649,535 | 3/1972 | Clark et al. | 428/374 |
| 3,788,852 | 1/1974 | Sels et al. | 430/539 |
| 3,960,780 | 6/1976 | Murata et al. | 510/351 |
| 5,043,089 | 8/1991 | Nollet et al. | 558/271 X |
| 5,252,770 | 10/1993 | Vanderlinde et al. | 558/271 |
| 5,547,820 | 8/1996 | Miyamoto | 430/523 |

FOREIGN PATENT DOCUMENTS 04-156933 5/1992 Japan .

OTHER PUBLICATIONS

File WPIDS on STN®, Derwent Information Ltd., (London, UK), Accession No. 92–231311, JP 04–156933, abstract, 1992.

*Primary Examiner*—Michael G. Ambrose
*Attorney, Agent, or Firm*—Richard S. Echler, Sr.; Kim William Zerby; Jacobus C. Rasser

[57] ABSTRACT

The present invention relates to anionic compounds and their application in detergent compositions. The compounds have the dual benefits of surfactancy and suds suppression.

20 Claims, No Drawings

DETERGENT COMPOSITIONS

TECHNICAL FIELD OF THE INVENTION

The present invention relates to detergent compositions comprising a surfactant which provides suds supressing benefits.

BACKGROUND OF THE INVENTION

There is a wide choice of surfactants currently available to the detergent manufacturer when formulating compositions in order to achieve the desired performance benefits.

A particularly desirable performance benefit for detergent compositions is good greasy and oily soil removal over a wide spectrum of temperatures. In order to achieve such desired performance benefits, the detergent manufacture has found it necessary to increase the amount of surfactant incorporated into detergent compositions. As a result the compositions have also tended to become more compact formulations, which is also in line with current trends to produce more compact formulations to reduce the environmental impact.

The sudsing profile of a detergent composition is also an important factor to be considered by the detergent manufacturer. It is generally considered that high sudsing is not a desirable feature of a laundry detergent composition for laundering conducted in automatic washing machines. However, high levels of surfactant in a detergent composition usually results in an increase in the sudsing of the detergent composition. This problem is particularly acute if the surfactant system comprises high levels of anionic surfactant. Thus, in order to control the suds profile, such compositions require the addition of a suds suppressor. However, the suds suppressors currently available are generally expensive and also provide no other performance benefit to the composition other than suds suppression. Therefore, it is desirable that their presence is minimised.

Thus, it is an aim of the present invention to provide a surfactant system which provides the dual performance benefits of excellent cleaning performance and providing suds suppression.

It has now been found that this objective can be achieved by the use of certain branched hydrolysable anionic compounds and detergent compositions as described herein. The anionic compounds of the present invention readily hydrolyse in the wash liquor and these hydrolysis products then act as suds suppressors. The hydrolysis products can thus act to suppress the sudsing produced by other surfactants which may be preferred components of the detergent composition. Of particular benefit is that the hydrolysis products tend to be formed in the latter stages of the washing process, when sudsing is at its greatest and suds suppression is most required. Furthermore, another advantage of the presence of the suds suppressing hydrolysis products, is that the amount of additional suds suppressor required in the formulation is reduced. Thus, the anionic compounds of the present invention have a dual function as a component of a surfactant system providing improved cleaning and as precursors of suds suppression agents in detergent compositions.

A further advantage of the anionic compounds of the present invention is that they are also low sudsing compounds per se.

Liquid detergent compositions comprising branched alkoxylated anionic surfactants for use as suds suppressors have been disclosed in European patent application number 93870123.2.

SUMMARY OF THE INVENTION

The present invention relates to compounds according to the formula:

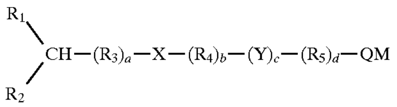

wherein $R_1$ and $R_2$ are independently $C_4$ to $C_{12}$ hydrocarbyl, X and Y are independently selected from

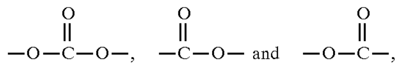

c is 0 or 1, $R_3$ and $R_4$ are independently $C_1$ to $C_4$ hydrocarbyl, a and b are independently from 0 to 4, $R_5$ is a $C_1$ to $C_9$ hydrocarbyl or $C_1$ to $C_9$ polyalkylene oxide having an average degree of polymerization of from 1 to 9, d is 0 to 2, Q is an anionic group, and M is a cation providing electrical neutrality and mixtures thereof.

The present invention also relates to detergent compositions comprising at least 0.1% of a compound according to any of the preceding claims and at least 0.1% of a detergent ingredient selected from surfactants builders and chelants and mixtures thereof.

The present invention also relates to a method of washing fabrics comprising contacting said fabrics with an aqueous solution comprising at least 0.005% of the compound or at least 0.1% of the detergent compositions of the present invention.

All percentages, ratios and parts as used herein are by weight unless otherwise specified.

DETAILED DESCRIPTION OF THE INVENTION

The Compound

The present invention is an anionic compound which provides the dual benefits of improved oily and greasy soil removal and of suds suppresion.

According to the present invention said compound is according to the formula:

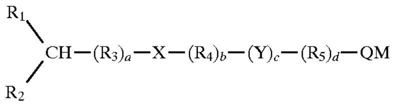

wherein $R_1$ and $R_2$ are independently $C_4$ to $C_{12}$, preferably $C_6$ to $C_{12}$, more preferably $C_6$ to $C_{10}$ hydrocarbyl, selected form alkyl, alkenyl and alkylaryl groups and which may be branched or linear. Preferably $R_1$ and $R_2$ are independently alkyl groups.

In a preferred embodiment of the compounds of the present invention the sum of the carbon chain lengths of $R_1$ and $R_2$ is from 10 to 18, more preferably from 12 to 18 and the difference in said carbon chain lengths of $R_1$ and $R_2$ is 4 or less, preferably 3 or less, most preferably 2 or less. In a most preferred embodiment $R_1$ and $R_2$ are independently $C_6$ to $C_{10}$ linear alkyl groups, most preferably having the same number of carbon atoms.

According to the present invention X and Y are independently selected from

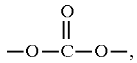,
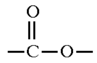
and
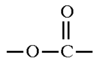

and c is 0 or 1, preferably zero.

According to the present invention $R_3$ and $R_4$ are independently $C_1$ to $C_4$, preferably linear $C_1$ to $C_2$ hydrocarbyl. a and b are independently from 0 to 4, preferably from 0 to 2.

$R_5$ is a $C_1$ to $C_{18}$, preferably a $C_1$ to $C_9$ hydrocarbyl selected from alkyls, alkenyls, and alkylaryls, or a $C_1$ to $C_9$ polyalkylene oxide, preferably ethylene or propylene having an average degree of polymerization of from 1 to 9, and d is 0 to 2.

According to the present invention Q is any anionic group. Suitable anionic groups for use herein may be selected from sulphates, sulphonates and carboxylates.

The compositions of the present invention are preferably substantially free of compounds containing about 13 or more ethylene oxide groups. These compounds tend to be relatively non-biodegradable, do not enhance the cleaning or fabric conditioning benefits provided by the compositions and may, in some circumstances, decrease the overall laundering performance provided by them. It is to be noted that polyethoxylated surfactants having relatively low levels of ethoxylation, such as those described above, exhibit better biodegradability characteristics and may be advantageously included in the compositions of the present invention.

M is a counter ion and may be any cation which results in the compound becoming water dispersible. The counterions are present in an appropriate number to give electrical neutrality.

Suitable cations may be selected from metal ions such as sodium, potassium, lithium, calcium, magnesium, ammonium or substituted ammonium. Specific examples of substituted ammonium cations include methyl-, dimethyl-, trimethyl-ammonium and quaternary ammonium cations such as tetramethylammonium, dimethylpiperidinium and cations derived from alkanolamines e.g. monoethanolamine, diethanolamine and triethanolamine and mixtures thereof.

Preferred anionic surfactants for use herein are according to the formulae:

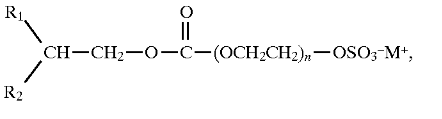,

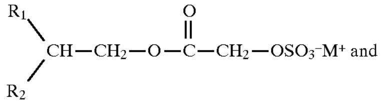
and

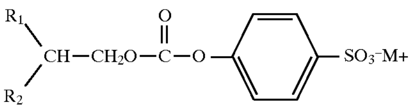

According to the present invention the anionic surfactants can be synthesised by methods known in the art.

EXAMPLE I

Preparation of $C_{12}$–$C_{16}$ Sulphophenyl Carbonate Ester Sodium $C_{12}$–$C_{16}$ Guerbetoxycarbonyloxybenzene Sulphonate

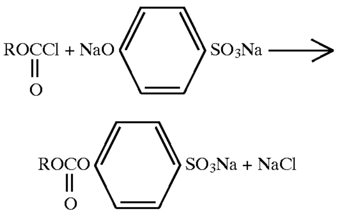

13 g of disodium phenolsulphonate (0.06 mole) and 100 ml of 2-methoxyethyl ether (diglyme) were placed in a 250 ml conical flask fitted with a magnetic stirrer and set for distillation. With stirring, using an oil bath as heat source, 20 ml of distillate was removed from the flask as a means of removing any unwanted moisture that may have been present. After cooling to 20° C., 20 g of Isofol 14T chloroformate (0.073 mole) was added to the conical flask and it was set for reflux. The resulting reaction mixture was heated to 100° C., and stirred at that temperature for 2 hours. After cooling to 20° C., the conical flask was filled to capacity with diethyl ether, refrigerated at 0° C. overnight and the precipitated by-product sodium chloride removed by centrifugation and decantation. The diglyme and ether were removed by means of a rotary vacuum evaporator to yield a crude, solid, product which was purified by recrystallisation from 40°–60° C. petroleum ether. This yielded 14.8 g of solid product which was characterised by proton NMR spectroscopy and shown to be 90.9% pure by Cat $SO_3$ titration.

According to another aspect of the present invention the anionic surfactants undergo hydrolysis at the ester or carbonate ester linkage, during the wash process yielding the corresponding fatty acids or alcohols. These hydrolysis products also act as suds suppressors.

Detergent Compositions

Another embodiment of the present invention is a detergent composition comprising at least 0.1%, preferably from 0.5% to 40%, most preferably from 0.5% to 20% of the compound of the present invention and at least 0.1%, preferably from 3% to 99.9% of a detergent ingredient selected from surfactants, builders, chelants and mixtures thereof.

Detersive Surfactants

According to the present invention the detergent composition may preferalby comprise surfactants. Surfactants useful herein include the conventional $C_{11}$–$C_{18}$ alkyl benzene sulphonates ("LAS") and primary, branched-chain and random $C_{10}$–$C_{20}$ alkyl sulphates ("AS"), the $C_{10}$–$C_{18}$ secondary (2,3) alkyl sulphates of the formula $CH_3(CH_2)_x(CHOSO_3^-M^+)$ $CH_3$ and $CH_3$ $(CH_2)_y(CHOSO_3^-M^+)$ $CH_2CH_3$ where x and (y+1) are integers of at least about 7, preferably at least about 9, and M is a water-solubilizing cation, especially sodium, unsaturated sulphates such as oleyl sulphate, the $C_{10}$–$C_{18}$ alkyl alkoxy sulphates ("$AE_xS$"; especially EO 1–7 ethoxy sulphates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulphated polyglycosides, and $C_{12}$–$C_{18}$ alpha-sulphonated fatty acid esters.

If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulphobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants such as cationics are listed in standard texts.

According to the present invention the compositions comprise from 1% to 80%, preferably from 5% to 50%, most preferably from 10% to 40% of a surfactant. Preferred surfactants for use herein are linear alkyl benzene sulphonate, alkyl sulphates and alkyl alkoxylated nonionics or mixtures thereof.

Builders

Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least 1% builder. Liquid formulations typically comprise from 5% to 50%, more typically about 5% to 30%, by weight, of detergent builder. Granular formulations typically comprise from 10% to 80%, more typically from 15% to 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, orthophosphates and glassy polymeric meta-phosphates), phosphonates, phytic acid, silicates, carbonates (including bicarbonates and sesquicarbonates), sulphates, and aluminosilicates (see, for example, U.S. Pat. Nos. 3,159,581; 3,213,030; 3,422,021; 3,400,148 and 3,422,137).

However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2Si_2O_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}\cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2Si_2O_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$M_z[(SiO_2)_w(zAlO_2)_y].xH_2O$$

wherein w, z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

$$Na_{12}[(AlO_2)_{12}(SiO_2)_{12}].xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al. on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at least low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from 0.1% to 10% more preferably, from 0.1% to 3.0% by weight of such compositions.

Bleaching Compounds—Bleaching Agents and Bleach Activators

The detergent compositions herein may optionally contain bleaching agents or bleaching compositions containing a bleaching agent and one or more bleach activators. When present, bleaching agents will typically be at levels of from 1% to 30%, more typically from 5% to 20%, of the detergent composition, especially for fabric laundering. If present, the amount of bleach activators will typically be from 0.1% to 60%, more typically from 0.5% to 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Mixtures of bleaching agents can also be used. Peroxygen bleaching agents, the perborates, e.g., sodium perborate (e.g., mono- or tetra-hydrate), the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

$$R^1N(R^5)C(O)R^2C(O)L$$

or $$R^1C(O)N(R^5)R^2C(O)L$$

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl)-oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

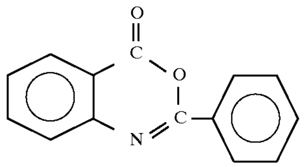
.

Still another class of preferred bleach activators includes the acyl lactam activators, especially acyl caprolactams and acyl valerolactams of the formulae:

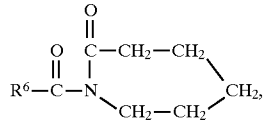

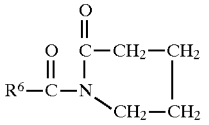

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from 0.025% to 1.25%, by weight, of such bleaches, especially sulfonate zinc phthalocyanine.

If desired, the bleaching compounds can be catalyzed by means of a manganese compound. Such compounds are well known in the art and include, for example, the manganese-based catalysts disclosed in U.S. Pat. No. 5,246,621, U.S. Pat. No. 5,244,594; U.S. Pat. No. 5,194,416; U.S. Pat. No. 5,114,606; and European Pat. App. Pub. Nos. 549,271A1, 549,272A1, 544,440A2, and 544,490A1; Preferred examples of these catalysts include $Mn^{IV}_2(u\text{-}O)_3(1,4,7\text{-trimethyl-}1,4,7\text{-triazacyclononane})_2(PF_6)_2$, $Mn^{III}_2(u\text{-}O)_1(u\text{-}OAc)_2(1,4,7\text{-trimethyl-}1,4,7\text{-triazacyclononane})_2(ClO_4)_2$, $Mn^{IV}_4(u\text{-}O)_6(1,4,7\text{-triazacyclononane})_4(ClO_4)_4$, $Mn^{III}Mn^{IV}_4(u\text{-}O)_1(u\text{-}OAc)_2\text{-}(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. No. 4,430,243 and U.S. Pat. No. 5,114,611. The use of manganese with various complex ligands to enhance bleaching is also reported in the following U.S. patents: U.S. Pat. Nos. 4,728,455; 5,284,944; 5,246,612; 5,256,779; 5,280,117; 5,274,147; 5,153,161; 5,227,084;

Polymeric Soil Release Agent

Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably polyvinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O$—, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units contains 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoarolyl, end-capped terephthalate esters.

If utilized, soil release agents will generally comprise from 0.01% to 10.0%, by weight, of the detergent compositions herein, typically from 0.1% to 5%, preferably from 0.2% to 3.0%.

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from 0.5% to 20%, by weight of the oligomer, of a crystalline-reducing stabilizer, preferably selected from the group consisting of xylene sulfonate, cumene sulfonate, toluene sulfonate, and mixtures thereof.

Clay Soil Removal/Anti-redeposition Agents

The compositions of the present invention can also optionally contain water-soluble ethoxylated amines having clay soil removal and antiredeposition properties. Granular detergent compositions which contain these compounds typically contain from 0.01% to 10.0% by weight of the water-soluble ethoxylates amines; liquid detergent compositions typically contain 0.01% to 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti redeposition agents known in the art can also be utilized in the compositions herein. Another type of preferred antiredeposition agent includes the carboxy methyl cellulose (CMC) materials. These materials are well known in the art.

Polymeric Dispersing Agents

Polymeric dispersing agents can advantageously be utilized at levels from 0.1% to 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders. Dispersing agents such as polyaspartate preferably have a molecular weight (avg.) of about 10,000.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from 0.01% to 10% by weight of the composition, preferably from 0.01% to 5%, and more preferably from 0.05% to 2%.

More specifically, the polyamine N-oxide polymers preferred for use herein contain units having the following structural formula: R-$A_x$-P; wherein P is a polymerizable unit to which an N—O group can be attached or the N—O group can form part of the polymerizable unit or the N—O group can be attached to both units; A is one of the following structures: — NC(O)—, —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

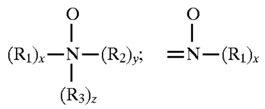

wherein $R_1$, $R_2$, $R_3$ are aliphatic, aromatic, heterocyclic or alicyclic groups or combinations thereof; x, y and z are 0 or 1; and the nitrogen of the N—O group can be attached or form part of any of the aforementioned groups. The amine oxide unit of the polyamine N-oxides has a pKa<10, preferably pKa<7, more preferred pKa<6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis,* Vol 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from 0.005% to 5% by weight of certain types of hydrophilic optical brighteners which also provide a dye transfer inhibition action. If used, the compositions herein will preferably comprise from 0.01% to 1% by weight of such optical brighteners.

The hydrophilic optical brighteners useful in the present invention are those having the structural formula:

ener species is commercially marketed under the tradename Tinopal AMS-GX by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal SBM-GX and/or Tinopal AMS-GX) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulations.

According to the present invention the detergent composition may comprise any other ingredients commonly employed in conventional detergent compositions such as

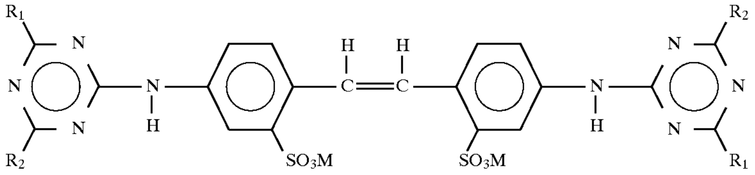

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightsoaps, suds suppressors, dye transfer inhibitors, perfumes, softeners, brighteners, enzymes and enzyme stabilisers.

The detergent compositions, which may be in granular, liquid or bar form, may be prepared by combining the ingredients in the required amounts in any suitable order by conventional means. When formulated as free following particles, i.e in powdered or granulated form, any conventional technique employed in the manufacture of detergent compositions may be used. To prevent premature hydrolysis of the compounds of the present invention in the formulation prior to washing, the maintenance of elevated temperatures under alkaline aqueous conditions should be avoided. Consequently, dry-mixing, agglomeration, granulation and extrusion techniques are preferable means of producing free flowing particle compositions.

A further aspect of the present invention is a method of washing fabrics wherein fabrics are contacted with an aqueous solution comprising at least 0.005% of the compound of the present invention or at least 0.1% of the detergent composition of the present invention.

EXAMPLES

The granular detergent compositions given in examples 1–10 are prepared by combining the listed ingredients in the given proportions.

| Composition in % | 1 | 2 | 3 |
|---|---|---|---|
| Zeolite A | 30 | 22 | 6 |
| $Na_2$ sulphate | 19 | 16 | 7 |
| Carboxylated polymer | 3 | 3 | 6 |
| LAS | 10 | 9 | 16 |
| 45AS | 8 | 7 | 7 |
| 45AE7 | 1 | 1 | 1 |
| Soap | — | — | 2 |
| Anionic compound according to Example I according to Example I | 4 | 3 | 6 |
| $Na_2$ silicate | — | 1 | 5 |
| $Na_2$ carbonate | 8 | 16 | 20 |
| brightener | 0.2 | 0.2 | 0.2 |
| DTPMP | — | 0.4 | 0.4 |
| PVP | 0.5 | 0.5 | 0.5 |
| Savinase ™ (4 KNPU/g) | 1 | 1 | 1 |
| Lipolase ™ 100 LU/g | 0.4 | 0.4 | 0.4 |
| NOBS | — | 6.1 | 4.5 |
| PB1 | 1 | 0.5 | 6 |
| Balance | 100 | 100 | 100 |

| Composition in % | 4 | 5 |
|---|---|---|
| Zeolite A | 23 | 23 |
| $Na_2$ citrate | 5 | — |
| $Na_2SO_4$ | — | 8 |
| LAS | 6.5 | 8 |
| TAS | 2 | 2 |
| Anionic compound according to Example I | 1.5 | 1.5 |
| $C_{14}$–$C_{15}$AE7 | 2 | 2 |
| $C_{14}$–$C_{15}$AE3 | 2 | — |
| DTPMP | 0.4 | 0.4 |
| CMC | 0.4 | 0.4 |
| Carboxylated polymer | 4 | 2 |
| $Na_2$ silicate | 3 | 3 |
| $Na_2$ carbonate | 16 | 23 |
| Na bicarbonate | — | 3 |
| TAED | 6 | 2 |
| $PB_1$ | 6 | 2 |
| Savinase ® 4 KNPU/g | 1 | 1 |
| Lipolase ® 100 LU/l | 0.4 | 0.4 |
| Termamyl ® 60 KNU/g | 0.6 | 0.6 |
| Carezyme ® | 0.6 | 0.6 |
| Silicone antifoam granule | 4 | 4 |
| Perfume | 0.3 | 0.3 |
| Balance | 100 | 100 |

| Composition in % | 6 | 7 | 8 |
|---|---|---|---|
| Zeolite A | 25 | 30 | 13 |
| SKS6 | — | — | 12 |
| $Na_2$ citrate | 10 | — | 8 |
| DTPMP | 0.4 | 0.5 | — |
| CMC | 0.4 | 0.4 | 0.5 |
| Carboxylated polymer | 4 | 4 | 5 |
| $C_{14}$–$C_{15}$AS | — | — | 9 |
| LAS | 7.5 | 6.5 | — |
| TAS | 3 | 2 | — |
| Anionic compound according to Example I | 1.5 | 1.5 | 2 |
| $C_{14}$–$C_{15}$AE7 | 4 | 4 | 4 |
| $C_{14}$–$C_{15}$AE3 | 2 | 2 | 2 |
| $Na_2$ silicate | 4 | 4 | — |
| $Na_2$ carbonate | 17 | 12 | 14 |
| Na bicarbonate | 7 | 3 | 5 |
| PVP | 0.5 | 0.5 | 0.5 |
| Savinase ® 4 KNPU/g | 1 | 1 | 1.3 |
| Lipolase ® 100 LU/l | 0.4 | 0.4 | 0.4 |
| Termamyl ® 60 KNU/g | 0.6 | 0.6 | 0.6 |
| Carezyme ® | 0.6 | 0.6 | 0.6 |
| Silicone antifoam granule | 4 | 4 | 4 |
| $Na_2$ sulphate | — | 14 | — |
| Perfume | 0.3 | 0.3 | 0.5 |
| Balance | 100 | 100 | 100 |

-continued

| Composition in % | 9 | 10 |
|---|---|---|
| STPP | 24 | — |
| Zeolite A | — | 24 |
| $Na_2$ sulphate | 12 | 9 |
| Carboxylated polymer | 2 | 4 |
| LAS | 4 | 6 |
| TAS | 2 | — |
| $C_{14}$–$C_{15}$AE7 | 2.5 | 2.5 |
| $C_{14}$–$C_{15}$AE3 | 2.5 | 2.5 |
| Anionic surfactant 2 according to example I | 2 | 2 |
| CMC | 1 | 1 |
| Brightener | 0.2 | 0.2 |
| DTPMP | 0.4 | 0.4 |
| Soap | 1 | 1 |
| Silicone suds suppressor | 0.2 | 0.2 |
| $Na_2$ silicate | 7 | 3 |
| $Na_2$ carbonate | 6 | 13 |
| $PB_4$ | 18 | 18 |
| $PB_1$ | 4 | 4 |
| TAED | 3 | 3 |
| Zinc phtalocyanine encapsulate | 0.02 | 0.02 |
| Savinase ® 4 KNPU/g | 1 | 1 |
| Lipolase ® 100 LU/l | 0.4 | 0.4 |
| Perfume | 0.3 | 0.3 |
| Balance | 100 | 100 |

We claim:

1. A compound according to the formula:

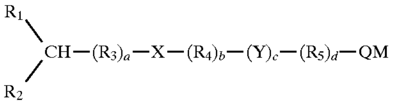

wherein $R_1$ and $R_2$ are independently $C_4$ to $C_{12}$ hydrocarbyl and the sum of the carbon chain lengths of $R_1$ and $R_2$ is from 10 to 18, X is selected from

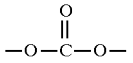 and 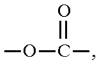

Y is selected from

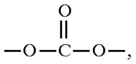 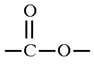 and 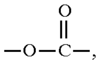

c is 0 or 1, $R_3$ and $R_4$ are independently linear $C_1$ to $C_2$ hydrocarbyl, a and b are independently from 0 to 4, $R_5$ is a $C_1$ to $C_9$ polyalkylene oxide having an average degree of polymerization of from 1 to 9, d is from 0 to 2, Q is an anionic group, and M is a cation providing electrical neutrality.

2. A compound according to claim 1, wherein the difference in the carbon chain lengths of $R_1$ and $R_2$ is 4 or less.

3. A compound according to claim 1, wherein $R_1$ and $R_2$ are independently selected from alkyl, alkenyl and alkylaryl groups.

4. A compound according to claim 1, wherein $R_1$ and $R_2$ are substantially linear.

5. A compound according to claim 1, wherein $R_1$ and $R_2$ are alkyl groups having the same number of carbon atoms.

6. A compound according to claim 1, wherein $R_3$ is $CH_2$ and a is 1.

7. A compound according to claim 6, wherein $R_5$ is a polyethylene oxide.

8. A compound according to claim 1, of the formula

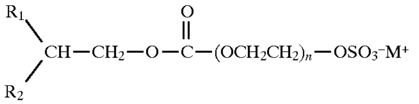

wherein n is from 1 to 9.

9. A detergent composition, comprising (a) at least 0.1 weight percent of a compound of the formula

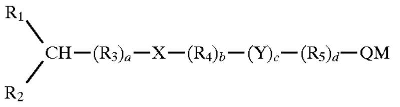

wherein $R_1$ and $R_2$ are independently $C_4$ to $C_{12}$ hydrocarbyl and the sum of the carbon chain lengths of $R_1$ and $R_2$ is from 10 to 18, X is selected from

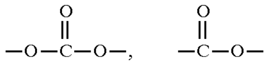

and

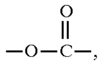

Y is selected from

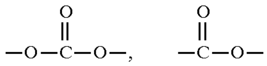

and

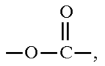

c is 0 or 1, $R_3$ and $R_4$ are independently $C_1$ to $C_4$ hydrocarbyl, a and b are independently from 0 to 4, $R_5$ is a $C_1$ to $C_9$ alkyl or alkenyl or a $C_1$ to $C_9$ polyalkylene oxide having an average degree of polymerization of from 1 to 9, d is from 0 to 2, Q is an anionic group, and M is a cation providing electrical neutrality, and (b) at least 0.1% of an additional detergent ingredient comprising detersive surfactant, builder, chelant or mixtures thereof.

10. A detergent composition according to claim 9, comprising from 0.5% to 40% of the compound (a).

11. A detergent composition according to claim 9 comprising from 1% to 80% of the surfactant (b).

12. A detergent composition according to claim 11, wherein the surfactant (b) comprises linear alkyl benzene sulphonate, alkyl sulphate, alkyl alkoxylated nonionic surfactant, or mixtures thereof.

13. A detergent composition according to claim 9, wherein the builder (b) comprises polycarboxylate builder, aluminosilicate builder or mixtures thereof.

14. A detergent composition according to claim 10, comprising a surfactant (b) and a builder (b), wherein the surfactant comprises linear alkyl benzene sulphonate, alkyl sulphate, alkyl alkoxylated nonionic surfactant, or mixtures thereof and wherein the builder comprises polycarboxylate builder, aluminosilicate builder or mixtures thereof.

15. A detergent composition according to claim 14, further comprising a percarbonate bleach.

16. A detergent composition according to claim 9, wherein in the compound (a), $R_3$ is $CH_2$ and a is 1.

17. A detergent composition according to claim 9, wherein in the compound (a), $R_5$ is polyethylene oxide or $CH_2$.

18. A method of suppressing sudsing in a fabric washing process, comprising washing the fabric with a detergent composition comprising (a) at least 0.1 weight percent of a compound of the formula

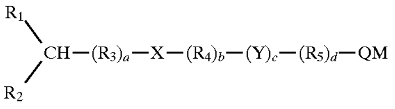

wherein $R_1$ and $R_2$ are independently $C_4$ to $C_{12}$ hydrocarbyl and the sum of the carbon chain lengths of $R_1$ and $R_2$ is from 10 to 18, X is selected from

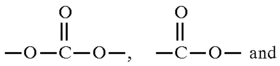

and

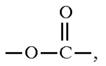

Y is selected from

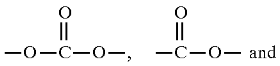

and

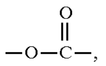

c is 0 or 1, $R_3$ and $R_4$ are independently $C_1$ to $C_4$ hydrocarbyl, a and b are independently from 0 to 4, $R_5$ is a $C_1$ to $C_{18}$ hydrocarbyl or a $C_1$ to $C_9$ polyalkylene oxide having an average degree of polymerization of from 1 to 9, d is from 0 to 2, Q is an anionic group, and M is a cation providing electrical neutrality, and (b) at least 0.1% of an additional detergent ingredient comprising detersive surfactant, builder, chelant or mixtures thereof.

19. A method according to claim 18, wherein the detergent composition comprises a surfactant (b) comprising linear alkyl benzene sulphonate, alkyl sulphate, alkyl alkoxylated nonionic surfactant, or mixtures thereof.

20. A method according to claim 19, wherein the detergent composition further comprises a builder (b) comprising polycarboxylate builder, aluminosilicate builder, or mixtures thereof.

* * * * *